United States Patent [19]

Hakky et al.

[11] Patent Number: 5,976,068

[45] Date of Patent: Nov. 2, 1999

[54] FEMALE URINARY INCONTINENCE DEVICE

[75] Inventors: Said I. Hakky, Largo; Perry B. Hudson, Seminole; A-Hamid Hakki, Largo, all of Fla.

[73] Assignee: 3H Inc., Largo, Fla.

[21] Appl. No.: 09/046,099

[22] Filed: Mar. 23, 1998

[51] Int. Cl.[6] ........................................... A61F 2/00
[52] U.S. Cl. ................................................. 600/29
[58] Field of Search ..................... 600/29–31; 128/885

[56] References Cited

U.S. PATENT DOCUMENTS

| | | | |
|---|---|---|---|
| 5,114,398 | 5/1992 | Trick et al. ............................. | 600/29 |
| 5,234,409 | 8/1993 | Goldberg et al. ....................... | 604/96 |
| 5,483,976 | 1/1996 | McLaughlin et al. .................. | 128/885 |
| 5,518,498 | 5/1996 | Lindenberg et al. .................... | 600/30 |
| 5,713,829 | 2/1998 | Hakky et al. ............................ | 600/29 |

Primary Examiner—Samuel Gilbert
Attorney, Agent, or Firm—Rosenberg, Klein & Bilker

[57] ABSTRACT

A female urinary incontinence device is provided for preventing uncontrolled flow of urine. The device is in the form of a hollow plastic tube having an open proximal end for insertion into the bladder and a control device at the distal for controlling the flow of urine. The proximal end has an extensible and retractable mushroom shaped plastic which maintains the device in the bladder.

3 Claims, 4 Drawing Sheets

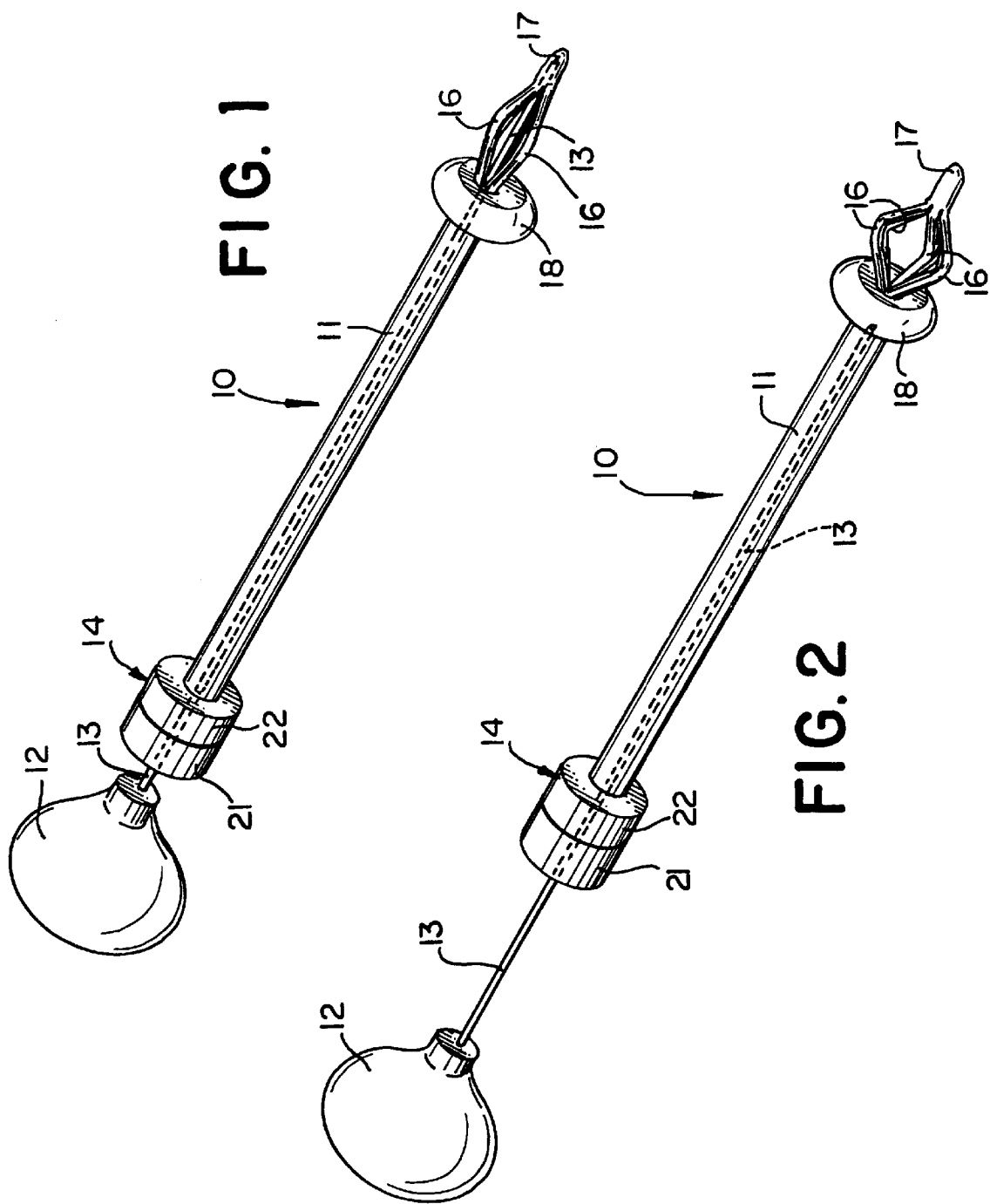

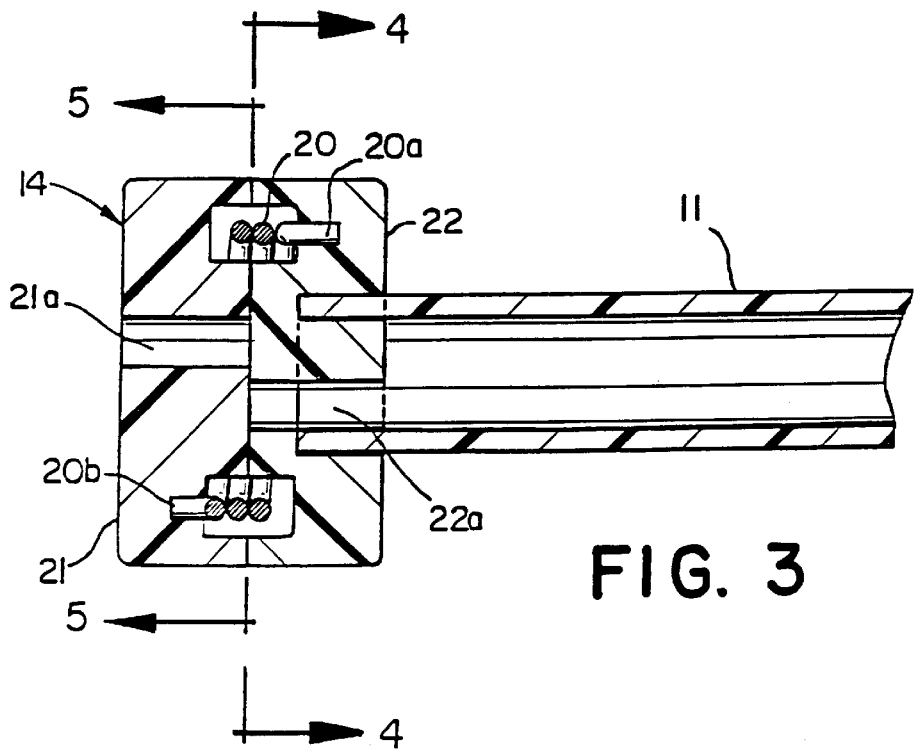
FIG. 3
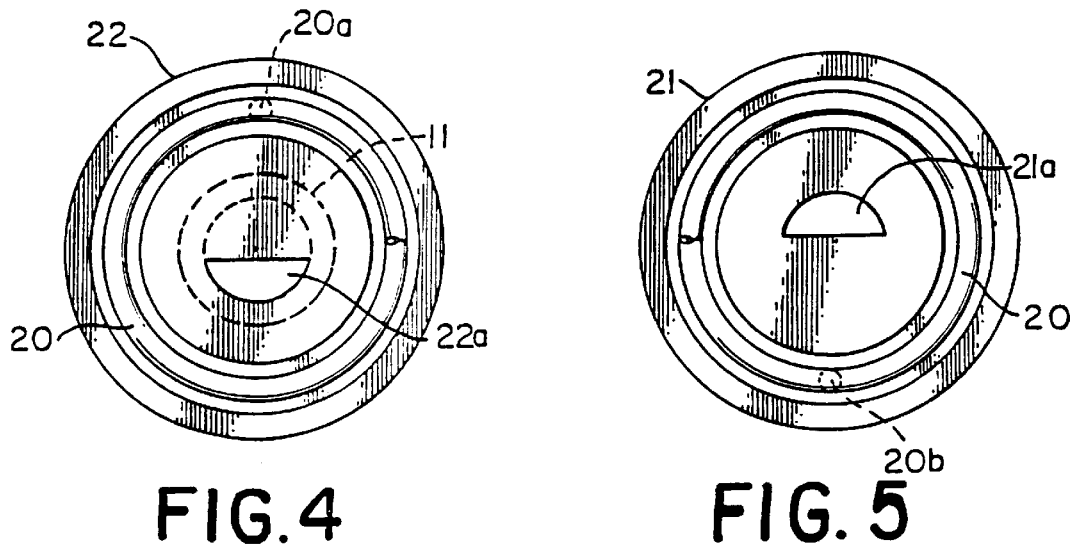
FIG. 4
FIG. 5

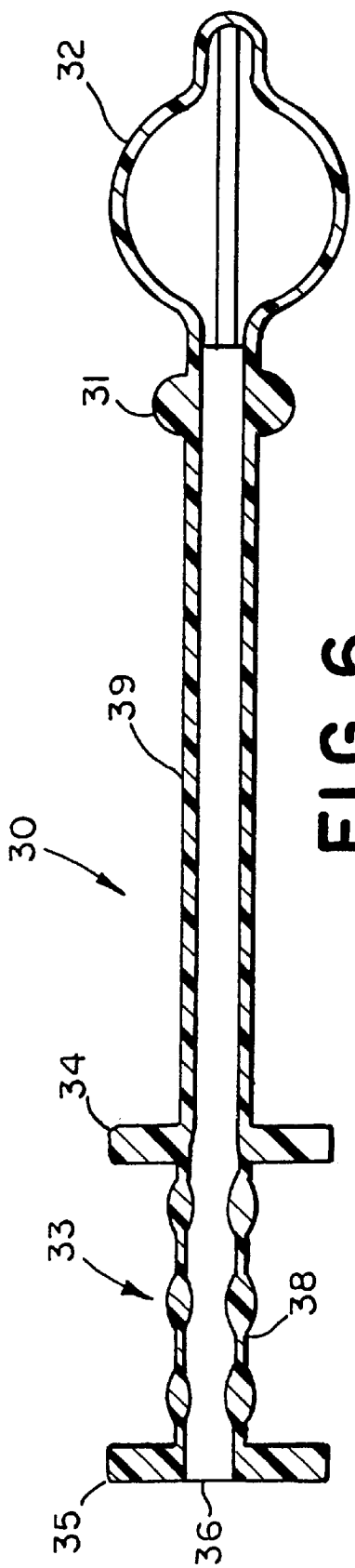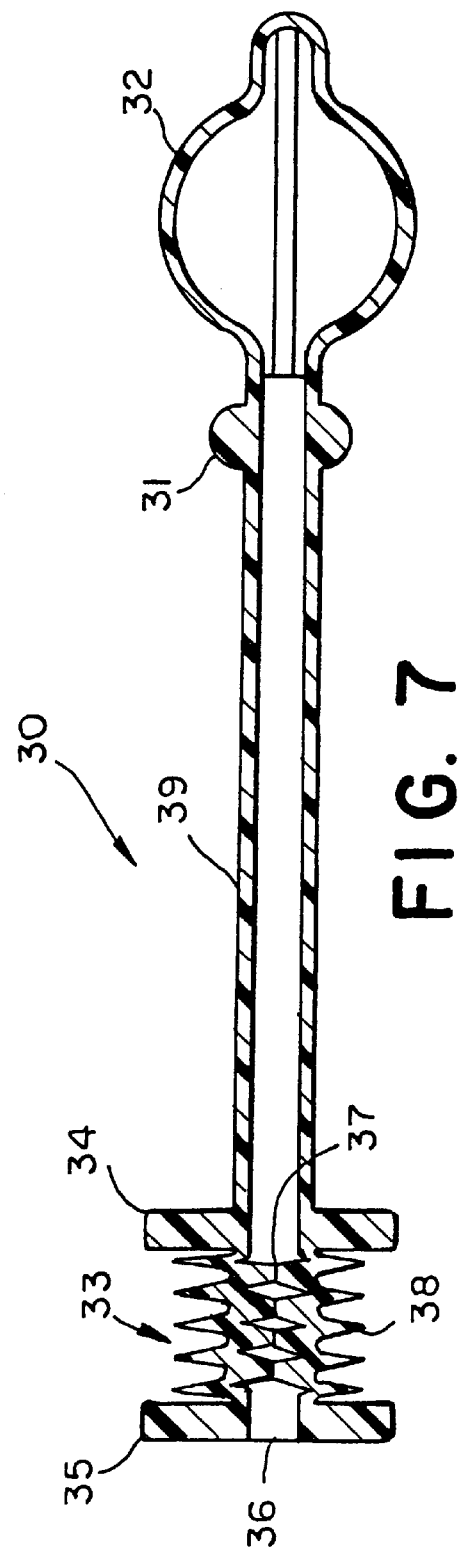

FEMALE URINARY INCONTINENCE DEVICE

FIELD OF THE INVENTION

The present invention relates to a female intraurethral urinary incontinence device. More particularly, there is provided a soft semi-collapsible urinary incontinence device which can be inserted and activated for drainage by the user.

BACKGROUND OF THE INVENTION

The female urethra is two inches long. It is situated between the two labia and at the entrance of the vaginal tract. It is anatomically difficult or impossible to place an external device on the urethra. In the male, the presence of the penis will facilitate placing an external device around the penis if the male patient is incontinent. Therefore, incontinent female patients uses pads or diapers to conceal their incontinence problem. Sometimes they have a permanent indwelling catheter. In young incontinent females, sexual intercourse is almost impossible.

It is therefore desirable to have a device that will prevent leakage of the urine, in addition, the female can have a normal life including intercourse, pregnancy and delivery without the smell of urine or the hazard of an indwelling catheter.

It is ideal that this device is soft and in a semi-collapsed state. The device thus will be less irritant and can be easily tolerated. The device should be completely concealed and does not interfere with sexual intercourse, pregnancy or delivery. The device should be easily inserted by the female patient, controlled by the patient and removed by the patient at any time she wishes to do so.

SUMMARY OF THE INVENTION

The present invention relates to a female urinary incontinence catheter or device. The device comprises a hollow tube having an open proximal end and an open distal end. At the proximal end is an extensible means for insertion and maintaining the device in the bladder. At the distal end is a means for controlling the flow of urine from the bladder. The control means comprises a valve which is normally closed to prevent the flow of urine and is manually opened to allow the flow of urine.

Advantageously, the valve means contains offset apertures which when aligned can permit urine flow or an insertion of a means for extending the maintenance means for inserting into the urinary tract.

Preferably, the hollow tube is soft and semi-collapsible so as to provide comfort for long periods of time.

It is a general object of the invention to provide a device for controlling female urinary incontinence.

It is another object of the invention to provide a female incontinence device which can be inserted and/or removed by the patient.

It is yet another object of this invention to provide a soft semi-collapsed catheter that is completely concealed by the incontinent female patient.

It is a further object of this invention to provide a hollow tube that drains the bladder by a mechanism activated by the female patient.

It is still a further object of this invention to provide a simple way to keep the catheter indwelling and could be removed by the female patient at any time she wishes to do so.

It is yet another object of this invention to provide methods to minimize and prevent the migration of the device into the bladder.

These and other objects of the instant invention will become obvious from the description of the invention contained herein and more particularly with reference to the following detailed description of the invention and the drawings where like elements are referred to by like reference numbers.

BRIEF DESCRIPTION OF THE DRAWINGS

FIG. 1 is a perspective view of the female urinary incontinence device of the invention together with an applicator in an extended position;

FIG. 2 is the device of FIG. 1 in a retracted position;

FIG. 3 is a cross-sectional view of the mechanical timer control;

FIG. 4 is a top view of the timer control of FIG. 3;

FIG. 5 shows the bottom part of the timer control of FIG. 3;

FIG. 6 is a cross-sectional view of a female urinary incontinence device of the invention with a flow control valve in the open position;

FIG. 7 is a cross-sectional view of the device of FIG. 6 with the flow control valve in the closed position.

Figure 8:
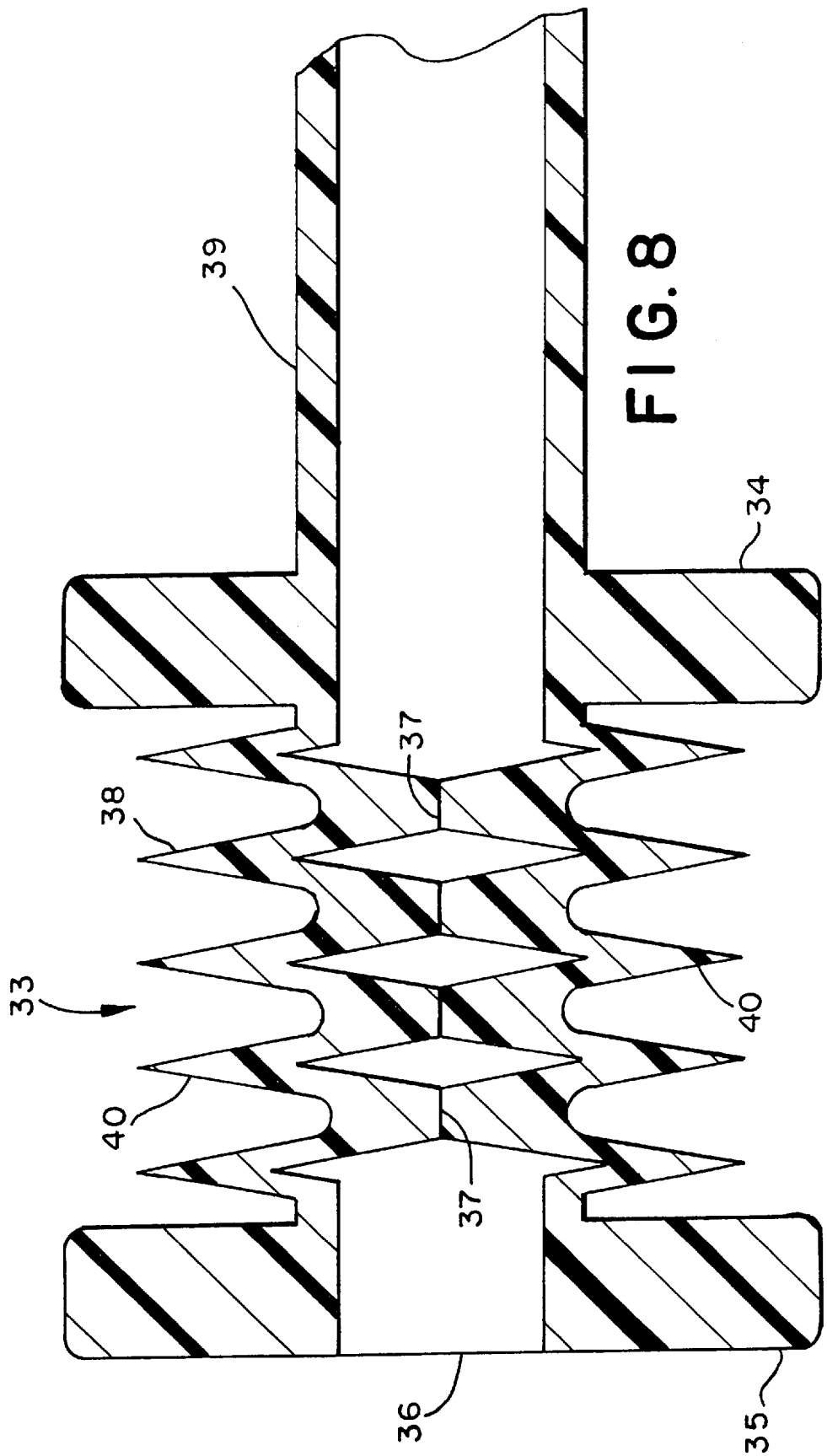
FIG. 8 is an enlarged cross-sectional view of the valve of FIG. 7.

The invention above has been described in connection with specific embodiments. It is to be understood, however that the particular descriptions contained herein is for the purpose of illustration and not for the purpose of limitation. Changes and modifications may be made to the description contained herein and still be within the scope of the claimed invention. Further, obvious changes and modifications will occur to those skilled in the art.

DESCRIPTION OF THE PREFERRED EMBODIMENTS

As shown in FIGS. 1 and 2, the female urinary incontinence catheter or device 10 has an elongated hollow tube 11. At the proximal end of the tube 11 is a flexible plastic member 16 which is normally in a retracted mushroom shape. The member 16 can be extended by use of an applicator 12 having a rod 13 which passes through the tube 11 and pushes against the reinforced tip 17 of the member 16. In the extended position the device 10 can be placed into the bladder. When she applicator 12 is removed the member 16 will retract into its normal balloon or mushroom shape and be maintained within the bladder. To remove the device 10 the patient reinserts the applicator into the tube 10 and extends member 16. Preferably, the rod 13 is hollow so that when the tip is inside the bladder urine will come out indicating that the proximal end is within the bladder.

At the proximal end of the tube 10 there is also a soft elastomeric seal 18 which prevents leakage from the bladder.

At the distal end of the tube 10 there is a urine control means 14 which is manually operated by the patient so as to permit the flow of urine out of the tube or to reinsert the applicator 12 to remove the device 10.

FIGS. 3–5 illustrate the control means 14 with a timing mechanism that can be formed by a rotating timing spring control valve or system 20 or other suitable valve which has a soft elastomeric coating. The timer control system 20 is constructed in two sections which contain two apertures 21a and 22a which are aligned as seen in FIG. 4 so as to allow urine to flow out of the tube or to insert the applicator 12 with the rod 13 therethrough. The part 21 can be manually rotated to place the aperture 21a in alignment with the aperture 22a on part 22. The timing spring 20 will rotate part 21 so that the apertures 21a and 22a are no longer aligned so as to close the system and prevent urine flow.

The outer portion of control means 14 and the seal 18 should be of soft elastomeric material so as to be comfortable for the patient when normally used and during sexual intercourse. Non-porous expanded polytetrafluoroethylene or similar material may be used. Pharmacological silicone or latex elastomers are other such elastomeric members which can be used.

The tube 11 should also be formed from a soft deformable plastic such as a polyolefin, i.e. polyethylene and polypropylene. The tube 11 may be fully collapsible but sufficiently open to permit urine flow.

The proximal end member 16 can be integral with the tube 11 or attached thereto. One form of the member 16 may be formed by cutting longitudinal slits in the tube and then providing the slits with a memory while in a retracted and mushroom shape such as by heating.

The applicator 12 can comprise a plastic or metal hollow rod which has a plastic gripping member on the end.

FIGS. 6–8 illustrate a female incontinence device 30 of the invention with a novel urine control valve 33. The device 30 has an elongated tube 39 having at the proximal end a flexible plastic member 32 which can be extended or retracted into a mushroom shape as shown. At the proximal end is also an elastomeric seal 31.

At the distal end of the tube 39 is the urine control valve 33. In FIG. 6, the valve 33 is shown in the open position with access into the tube 39 through opening 36 for insertion of the applicator 12. Generally, in the closed position the valve 33 is about one inch in length and in the closed position about ½ inch in length. The valve 33 has a pair of elastomeric seals 34, 35 and accordion type pleats 38, 40. As shown in FIG. 8, the pleats form a plurality of seals 37 along its length to prevent urine flow. The length of the device shown in FIG. 7 is generally about 3 to 4 inches.

Method Of Use

The device 10 can be inserted through the urethra into the bladder by the patient with the applicator 12 in position as shown in FIG. 1. When the device is sufficiently inserted urine will come out of the bladder. The applicator 12 is then removed and the control means 14 is moved into the closed position. The proximal end member 16 becomes mushroom shaped and prevents the device from shipping out of the bladder. When member 16 becomes mushroom shaped it forms the seal with the soft elastomeric sealing means 18. In order for the patient to empty her bladder she will manually activate the control means 14 so that there is an opening for the urine to flow. Preferably, the control means 14 comprises a timer as in FIGS. 3–5 which maintains the opening for the urine to flow 30 to 45 seconds.

The most preferred controlled valve system is seen in FIGS. 6 and 7. This accordion type of valve is simple to activate by merely separating two donut shape and soft elastomer 34, 35. This is important in patients with nervous disability. Another advantage of this preferred valve system is that when the pressure in the bladder rises to a dangerous level i.e., in patients who have no sensation, the valve will automatically open. This will prevent back pressure damage to the kidneys.

It is to be understood, however, that even though specific characteristics and advantages of the present invention have been set forth in the foregoing description, together with details of the structure and function of the invention, it will be appreciated that the disclosure is illustrative only, and that changes may be made in detail, especially in matters of shape, size, arrangement of parts or sequence or elements of events within the principles of the invention to the full extent indicated by the broad general meaning of the terms in which the appended claims are expressed.

What is claimed is:

1. A female urinary incontinence device to be placed in a patient's urinary tract, comprising:

a hollow plastic tube having an open proximal end and an open distal end;

an expandable member adjacent said proximal end for maintaining said device within the patient's bladder: and, an accordion type valve having a plurality of pleats and a valve passage and being disposed adjacent said distal end for controlling flow of urine from the patient's bladder through said valve passage, said valve being normally closed to prevent a flow of urine and manually opened to allow the flow of urine, said valve forming a plurality of seals in said valve passage when said valve is in a closed position.

2. The device of claim 1 wherein said plurality of pleats are disposed between a pair of elastomeric seals.

3. A female urinary incontinence device to be placed in a patient's urinary tract, comprising:

a hollow deformable soft plastic longitudinally extended tube having an open proximal end and an open distal end, said tube having an extensible mushroom shaped portion formed adjacent said proximal end for maintaining said device in the patient's bladder:

an elastomeric seal disposed adjacent said mushroom shaped portion of said tube for preventing leakage of urine from the patient's bladder:

a pair of elastomeric members disposed adjacent said distal end of said tube in longitudinally spaced relationship; and, an elastomeric manually operable urine control valve disposed between said pair of elastomeric members and having an open position and a closed position for controlling urine flow through a valve passage, said control valve including an accordion type pleated portion forming a plurality of seals in said valve passage responsive to said valve being in said closed position.

* * * * *